US008744870B2

(12) United States Patent
Shastri et al.

(10) Patent No.: US 8,744,870 B2
(45) Date of Patent: Jun. 3, 2014

(54) METHOD AND SYSTEM FOR FORECASTING CLINICAL PATHWAYS AND RESOURCE REQUIREMENTS

(75) Inventors: Lokendra Shastri, Bhopal (IN); Gopichand Agnihotram, Tenali (IN); Balasubramanian Kanagasabapathi, Erode (IN); Antony Arokia Durai Raj Kolandaiswamy, Pollachi (IN)

(73) Assignee: Infosys Limited (IN)

( * ) Notice: Subject to any disclaimer, the term of this patent is extended or adjusted under 35 U.S.C. 154(b) by 397 days.

(21) Appl. No.: 13/069,623

(22) Filed: Mar. 23, 2011

(65) Prior Publication Data

US 2012/0150498 A1 Jun. 14, 2012

(30) Foreign Application Priority Data

Dec. 10, 2010 (IN) .............. 3780/CHE/2010

(51) Int. Cl.
*G06Q 10/00* (2012.01)
*G06Q 50/00* (2012.01)
*G06Q 50/22* (2012.01)
*G06Q 50/24* (2012.01)
*G06F 19/00* (2011.01)

(52) U.S. Cl.
CPC .............. *G06Q 50/22* (2013.01); *G06Q 50/24* (2013.01); *G06F 19/322* (2013.01)
USPC ................................. 705/2; 705/3

(58) Field of Classification Search
CPC ....... G06Q 50/22; G06Q 50/24; G06F 19/322
USPC .......................... 705/2–3; 600/300
See application file for complete search history.

(56) References Cited

U.S. PATENT DOCUMENTS

| | | | |
|---|---|---|---|
| 2009/0089092 A1* | 4/2009 | Johnson et al. | 705/2 |
| 2010/0011302 A1* | 1/2010 | Stein et al. | 715/753 |
| 2010/0174555 A1* | 7/2010 | Abraham-Fuchs et al. | 705/3 |
| 2011/0301977 A1* | 12/2011 | Belcher et al. | 705/3 |
| 2012/0065986 A1* | 3/2012 | Tesanovic et al. | 705/2 |

OTHER PUBLICATIONS

Uzark, Changing Practice Patterns for Children with Heart Disease: A Clinical Pathway Approach, Mar. 1998, American Journal of Critical Care, vol. 7, No. 2, pp. 101-105.*

* cited by examiner

*Primary Examiner* — Luke Gilligan
(74) *Attorney, Agent, or Firm* — Lerner, David, Littenberg, Krumholz & Mentlik, LLP

(57) ABSTRACT

A system, method and computer program product for forecasting one or more clinical pathways and resource requirements of at least one patient are provided. The system comprises an input module for receiving inputs pertaining to patient diagnostic data, the patient diagnostic data comprising information identified during diagnosis of the patient. The system also comprises a repository for storing data comprising at least one of patient data and pre-existing clinical pathways. The patient data comprises at least one of the patient diagnostic data received from the input module; patient historical data comprising historical treatment data of the patient and patient demographic data comprising demographic details of the patient. The system also comprises a clinical pathway forecasting module for forecasting clinical pathways by application of predetermined analytical models on the patient data and pre-existing clinical pathways. The system further comprises a resource requirement forecasting module for forecasting resource requirements of the patient.

36 Claims, 5 Drawing Sheets

METHOD AND SYSTEM FOR FORECASTING CLINICAL PATHWAYS AND RESOURCE REQUIREMENTS

FIELD OF INVENTION

The present invention relates generally to capacity management in the healthcare industry. More specifically, the present invention relates to forecasting clinical pathways and resource requirements, and generating schedules for patients and resources.

BACKGROUND OF THE INVENTION

In the healthcare industry, significant emphasis is provided to the management of resources. Forecasting and scheduling of resources are the key factors in efficient management of resources. Clinical pathways also referred to as care pathways, critical pathways, integrated care pathways or care maps, represent the sequence of medical procedures for treatment of patients. A clinical pathway is determined based on data gathered from outcome of medical examination and medical diagnostics of a patient.

Various models, based on queuing theory and simulation, are used for forecasting clinical pathways and managing resources in healthcare systems. These models focus on solving resource management problems, analyzing information flows within the healthcare systems, estimating resource requirements and so forth. Further, these models estimate the effect of demographic factors and service characteristics on capacity management in the healthcare systems. These estimates are used for cost reduction and service quality enhancement.

The models based on queuing theory provide solutions for problems with limited data and challenges related to randomness in data. These challenges are solved by making generic assumptions related to various constraints such as length of stay of patients, duration of medical procedures and so forth. The models based on simulation focus on identifying data complexity, identifying distribution of data, validating data, interpreting identified data and so forth.

Some models for forecasting clinical pathways consider patient specific data. For example, clinical pathways forecasted based on initial diagnosis consider the classification from the International Classification of Diseases (ICD) assigned during initial diagnosis of patients.

The models for forecasting clinical pathways and resource requirements have one or more of the following limitations. The models based on queuing theory and simulation do not provide efficient solutions for problems with data complexity. Also, substantial weight is not provided to data collection, data verification and data validation. The models that use ICD data do not consider the patient clinical and diagnostic data, available subsequent to medical procedures, for forecasting clinical pathways, thereby providing incorrect resource requirements forecasts.

Consequently, there is a need for a method and system for efficiently forecasting clinical pathways. Also, the method should enable efficient forecasting of resource requirements. Further, a method and system is required for optimal utilization of resources in healthcare organizations.

SUMMARY OF THE INVENTION

A system, computer-implemented method and computer program product for forecasting one or more clinical pathways and resource requirements of at least one patient are provided. In various embodiments of the present invention, the system comprises an input module. The input module, in communication with a computer system, is configured to receive inputs pertaining to patient diagnostic data. In an embodiment of the present invention, the patient diagnostic data comprises information identified during diagnosis of the patient.

The system further comprises a repository. The repository, in communication with the computer system, is configured to store data. In various embodiments of the present invention, the data comprises at least one of patient data and pre-existing clinical pathways. In an embodiment of the present invention, the patient data comprises at least one of the patient diagnostic data received from the input module; patient historical data comprising historical treatment data of the patient; and patient demographic data comprising demographic details of the patient.

The system also comprises a clinical pathway forecasting module. The clinical pathway forecasting module, in communication with the computer system, is configured to forecast one or more clinical pathways by application of one or more predetermined analytical models on the patient data and pre-existing clinical pathways.

In addition, the system comprises a resource requirement forecasting module. The resource requirement forecasting module, in communication with the computer system, is configured to forecast the resource requirements of the patient. In an embodiment of the present invention, resource requirements are forecasted based on the pre-existing clinical pathways, forecasted clinical pathways, historical treatment data of patients and one or more predetermined analytical models.

In an embodiment of the present invention, the clinical pathway forecasting module is configured to forecast an initial clinical pathway. The forecasting is performed based on at least one of information identified during the initial diagnosis of the patient; preliminary information gathered during the initial contact with the patient; and the pre-existing clinical pathways.

In another embodiment of the present invention, the clinical pathway forecasting module is configured to forecast the clinical pathways based on real-time data pertaining to the patient gathered via the input module.

In an embodiment of the present invention, the resource requirement forecasting module is configured to forecast the resource requirements. The forecasting is performed based on at least one of patient historical data; the pre-existing clinical pathways and forecasted clinical pathways; the initial forecasted clinical pathway; and at least one predetermined analytical model.

In an embodiment of the present invention, the system comprises an itinerary generation module. The itinerary generation module, in communication with the computer system, is configured to generate one or more itineraries based on at least one of the pre-existing clinical pathways and forecasted clinical pathways; the initial forecasted clinical pathway; the forecasted resource requirements; arrival time of the patient; average time taken by the patient to travel from one state to another state of the clinical pathway; time duration for performing procedures at each state; scheduled waiting times prior to performing procedures at each state; and at least one predetermined analytical model.

In various embodiment of the present invention, each itinerary comprises a schedule for treatment of the patient. In an embodiment of the present invention, the schedule for treatment of the patient is determined by calculating time required at one or more states of the clinical pathway. In another embodiment of the present invention, the schedule for treatment of the patient is used to determine at least one of waiting time of the patient at each state; number of patients using a resource at a given time instance; and utilization status of resources at a given time instance and utilization level of resources.

In various embodiments of the present invention, the generated itineraries are stored in the repository.

In an embodiment of the present invention, the itinerary generation module is configured to generate one or more itineraries for resources. Each itinerary for resources comprises at least one of utilization status of resources at a given time instance and utilization level of resources.

In various embodiments of the present invention, the system comprises a clinical pathway graph module. In an embodiment of the present invention, the clinical pathway graph module, in communication with the computer system, is configured to generate one or more clinical pathway graphs. Each graph represents a clinical pathway and comprises one or more nodes connected via one or more interconnections.

In another embodiment of the present invention, the clinical pathway graph module is further configured to generate one or more clinical pathway graphs for each forecasted clinical pathway.

In various embodiments of the present invention, each node of the clinical pathway graphs is at least one of a state node, an action node and a decision node. Each state node represents a state in the forecasted clinical pathway, the state node being associated with predefined state functions for ascertaining data recorded for the corresponding state. Each action node represents an action being performed, the action node being associated with at least one of a predefined information function and a predefined resource function corresponding to the action being performed. Each decision node representing a decision point in the forecasted clinical pathway, the decision node being associated with one or more predefined decision functions for determining subsequent states corresponding to the decision point.

In an embodiment of the present invention, the clinical pathway forecasting module, in communication with the computer system, is configured to compute at least one of probability of visiting each of the subsequent state nodes along one or more clinical pathways; predicted outcome; and value of dependent variables. The computations are performed at one or more nodes of the pre-existing clinical pathways and the forecasted clinical pathways.

In an embodiment of the present invention, the computations are performed to forecast one or more clinical pathways based on data available at one or more states of the clinical pathway.

In an embodiment of the present invention, the system comprises a forecasted clinical pathway repository. The forecasted clinical pathway repository, in communication with the computer system, is configured to store the forecasted clinical pathways.

In an embodiment of the present invention, the system comprises a clinical pathway repository. The clinical pathway repository, in communication with the computer system, is configured to store at least one of the pre-existing clinical pathways and one or more Standard Operating Procedures (SOPs). The pre-existing clinical pathways provide guidelines for treatment of diseases corresponding to a set of International Classification of Diseases (ICD) and the SOPs are defined for the set of ICD.

In an embodiment of the present invention, the system comprises a patient data repository. The patient data repository, in communication with the computer system, is configured to store the patient data.

In an embodiment of the present invention, at least one of the predetermined analytical models is adaptive.

In an embodiment of the present invention, the system for forecasting one or more clinical pathways comprises an input module, a repository and a clinical pathway forecasting module. The input module, in communication with the computer system, is configured to receive inputs pertaining to patient data. The repository, in communication with the computer system, is configured to store at least one of the patient data received from the input module and pre-existing clinical pathways. The clinical pathway forecasting module, in communication with the computer system, is configured to forecast one or more clinical pathways by the application of one or more predetermined analytical models on the received inputs and pre-existing clinical pathways.

The system further comprises a resource requirement forecasting module. The resource requirement forecasting module, in communication with the computer system, is configured to forecast the resource requirements of the patient based on the pre-existing clinical pathways, forecasted clinical pathways, historical treatment data of patients and one or more predetermined analytical models. The system also comprises an itinerary generation module. The itinerary generation module, in communication with the computer system, is configured to generate one or more itineraries. The itineraries are generated based on at least one of the pre-existing clinical pathways and forecasted clinical pathways; resource requirements of the patient; time duration for performing one or more treatment procedures; and at least one predetermined analytical model. Each itinerary comprises a schedule for treatment of the patient. In an embodiment of the present invention, the pre-existing clinical pathways provide guidelines for treatment of diseases corresponding to one or more International Classification of Diseases (ICD).

In various embodiments of the present invention, the computer-implemented method for forecasting one or more clinical pathways and resource requirements of at least one patient comprises gathering, using a computer system, inputs pertaining to patient data. In an embodiment of the present invention, the patient data comprises at least one of patient diagnostic data comprising information identified during diagnosis of the patient; patient historical data comprising historical treatment data of the patient; and patient demographic data comprising demographic details of the patient.

The method further comprises retrieving, using a computer system, pre-existing clinical pathways based on the gathered patient data. The method also comprises forecasting, using a computer system, one or more clinical pathways by application of one or more predetermined analytical models on the gathered patient data and retrieved pre-existing clinical pathways. In addition, the method comprises forecasting, using a computer system, the resource requirements of the patient based on the pre-existing clinical pathways, the forecasted clinical pathways, historical treatment data of patients and one or more predetermined analytical models.

In an embodiment of the present invention, the method comprises forecasting, using a computer system, the clinical pathways based on real-time data pertaining to the patient.

In an embodiment of the present invention, the method comprises storing, using a computer system, the forecasted clinical pathways.

In an embodiment of the present invention, the method comprises forecasting, using a computer system, an initial clinical pathway for the patient. The initial clinical pathway is forecasted based on at least one of information identified during the initial diagnosis of the patient; preliminary information gathered during the initial contact with the patient; and the pre-existing clinical pathways.

In an embodiment of the present invention, the method comprises generating, using a computer system, one or more itineraries for the patient based on at least one of the pre-existing clinical pathways and forecasted clinical pathways; the initial forecasted clinical pathway; the forecasted resource requirements; arrival time of the patient; average time taken by the patient to travel from one state to another state of the clinical pathway; time duration for performing procedures at each state; scheduled waiting times prior to performing procedures at each state; and at least one predetermined analytical model. Each itinerary comprises a schedule for treatment of the patient. In an embodiment of the present invention, the schedule for treatment of a patient is determined by forecasting time required at one or more states of the clinical pathway.

In various embodiments of the present invention, the computer program product comprising a computer usable medium having a computer-readable program code embodied thereon to forecast one or more clinical pathways and resource requirements of at least one patient, the computer-readable program code comprising instructions that, when executed by a computer system, cause the computer system to gather inputs pertaining to patient data. In an embodiment of the present invention, the patient data comprises at least one of patient diagnostic data comprising information identified during diagnosis of the patient; patient historical data comprising historical treatment data of the patient; and patient demographic data comprising demographic details of the patient. The computer program product further comprises instructions that, when executed by the computer system, cause the computer system to retrieve pre-existing clinical pathways based on the gathered patient data. The computer program product further comprises instructions that, when executed by the computer system, cause the computer system to forecast one or more clinical pathways by application of one or more predetermined analytical models on the gathered patient data and retrieved pre-existing clinical pathways. The computer program product further comprises instructions that, when executed by the computer system, cause the computer system to forecast the resource requirements of the patient based on the pre-existing clinical pathways, the forecasted clinical pathways, historical treatment data of patients and one or more predetermined analytical models.

In an embodiment of the present invention, the computer program product further comprises instructions that, when executed by the computer system, cause the computer system to forecast the clinical pathways based on real-time data pertaining to the patient.

In an embodiment of the present invention, the computer program product further comprises instructions that, when executed by the computer system, cause the computer system to store the forecasted clinical pathways.

In an embodiment of the present invention, the computer program product further comprises instructions that, when executed by the computer system, cause the computer system to forecast an initial clinical pathway for the patient based on at least one of information identified during the initial diagnosis of the patient; preliminary information gathered during the initial contact with the patient; and the pre-existing clinical pathways. The computer program product further comprises instructions that, when executed by the computer system, cause the computer system to generate one or more itineraries for the patient based on at least one of the pre-existing clinical pathways and forecasted clinical pathways; the initial forecasted clinical pathway; the forecasted resource requirements; arrival time of the patient; average time taken by the patient to travel from one state to another state of the clinical pathway; time duration for performing procedures at each state; scheduled waiting times prior to performing procedures at each state; and at least one predetermined analytical model.

In various embodiments of the present invention, each itinerary comprises a schedule for treatment of the patient. The schedule for treatment of a patient is determined by forecasting time required at one or more states of the clinical pathway.

BRIEF DESCRIPTION OF THE DRAWINGS

The present invention is described by way of embodiments illustrated in the accompanying drawings wherein.

DETAILED DESCRIPTION

The present invention provides a system and method for forecasting one or more clinical pathways. The method includes collecting patient data, wherein patient data includes patient historical data, patient demographic data and patient diagnostic data. Various analytical models such as, but not limited to, regression/time series models, neural network models, belief nets/Bayesian networks, decision trees and rule engines, are used for efficient forecasting of the clinical pathways. The method also includes generating an itinerary for the patient based on the forecasted clinical pathway. The itinerary provides details related to resource requirements of the patient. The itinerary also provides details related to the schedule of medical procedures for the patient.

The disclosure is provided in order to enable a person having ordinary skill in the art to practice the invention. Exemplary embodiments are provided only for illustrative purposes and various modifications will be readily apparent to persons skilled in the art. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

The present invention would now be discussed in context of embodiments as illustrated in the accompanying drawings.

Figure 1:
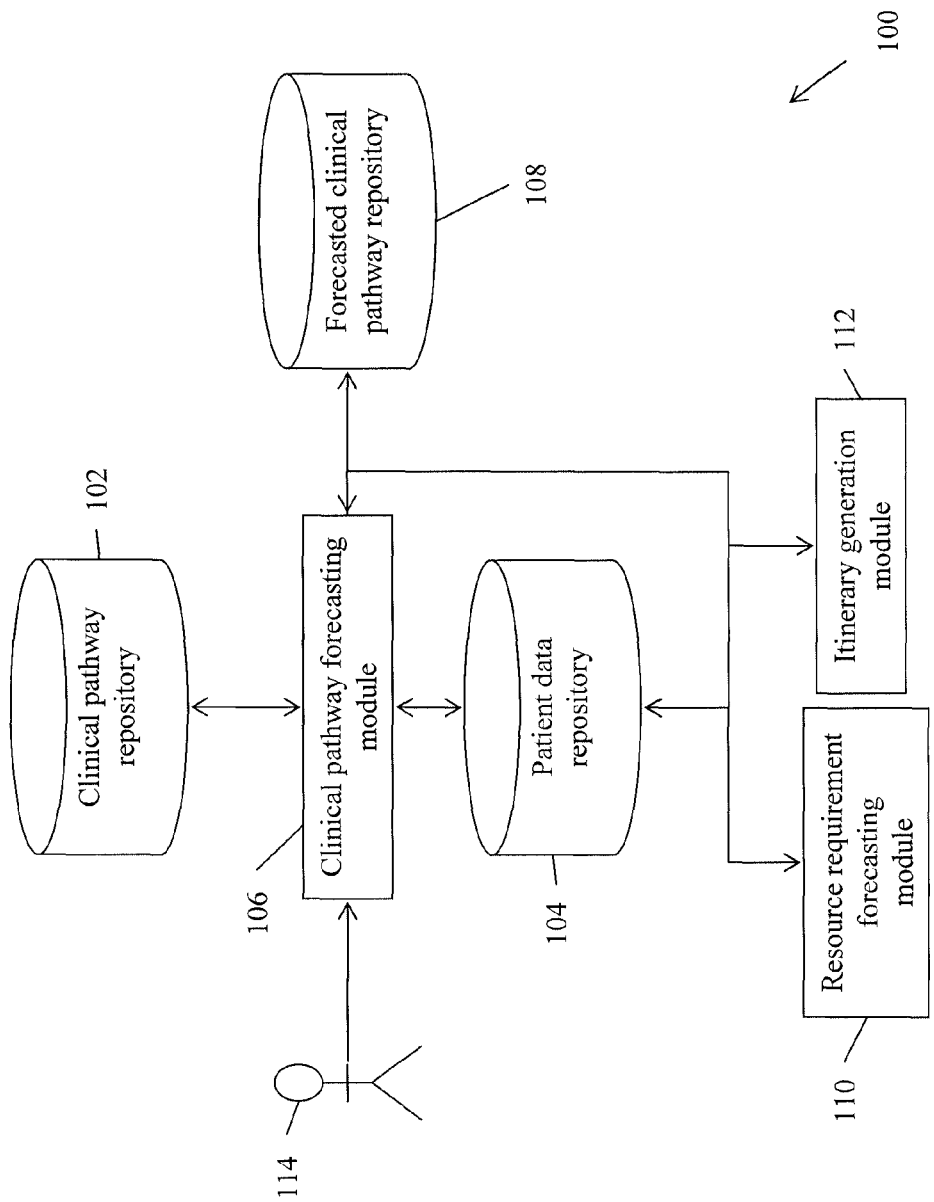
FIG. 1 is a block diagram of a system for forecasting one or more clinical pathways, in accordance with an embodiment of the present invention.

FIG. 1 is a block diagram of a system for forecasting one or more clinical pathways, in accordance with an embodiment of the present invention.

Clinical pathways also referred to as care pathways, critical pathways, integrated care pathways or care maps, represent the steps or sequence of medical procedures for treatment of patients. The medical procedures followed in treatment of diseases include, but are not limited to, medical examinations, medical diagnosis and medical treatments. A clinical pathway is determined based on data gathered from outcome of medical examination and medical diagnosis of a patient. The clinical pathways are used to forecast resource requirements for a patient, which in turn may be used to efficiently manage various resources present in a healthcare organization. Generally clinical pathways refer to medical guidelines.

In various embodiments of the present invention, a clinical pathway includes one or more states, wherein a state represents the stage of medical treatment of a patient. For example, the states in a clinical pathway for myocardial infarction represent the stages of patient healthcare status before diagnosis, electrocardiography, fibrinolysis and so forth. At each state one or more actions are performed and one or more decisions are made. For example, blood tests are performed in various states, X-rays images are captured in a chest X-ray examination state and so forth. Further, decisions such as whether the patient requires an electrocardiogram, whether a fibrinolysis should be performed and so forth, are made at various states.

In various embodiments of the present invention, clinical pathways are forecasted based on Standard Operating Procedures (SOPs) defined for classifications from the International Classification of Diseases (ICD). A standard operating procedure (SOP) is defined as the prescribed set of prerequisite procedures to be followed in order to treat the patient for an ICD. These procedures evolve over a period of time and are generally acceptable to many healthcare service providers. In general, a SOP acts as clinical guideline. Further, the SOP for a particular ICD consists of one or more pre-existing clinical pathways.

System 100 includes a clinical pathway repository 102, a patient data repository 104, a clinical pathway forecasting module 106, a forecasted clinical pathway repository 108, a resource requirement forecasting module 110 and an itinerary generation module 112. The clinical pathways are forecasted for patients such as patient 114.

Clinical pathway repository 102 is configured to store pre-existing clinical pathways. Patient data repository 104 is configured to store patient data and historical patient treatment data. Clinical pathway forecasting module 106 is configured to perform computations for forecasting one or more clinical pathways. Further, clinical pathway forecasting module 106 is configured to perform computations dynamically using pre-existing clinical pathways, predefined clinical pathway graphs, patient historical data, patient demographic data and patient diagnostic data. In various embodiments of the present invention, a clinical pathway graph corresponds to a clinical pathway and is a collection of nodes and interconnections, wherein nodes include state nodes, action nodes and decision nodes. Further, each node is associated with one or more functions defined based on various analytical models.

Forecasted clinical pathway repository 108 is configured to store the forecasted clinical pathways. Resource requirement forecasting module 110 is configured to forecast resource requirements based on the forecasted clinical pathways and resource requirement data associated with nodes in the clinical pathways. Itinerary generation module 112 is configured to generate itineraries based on the forecasted clinical pathways and historical patient treatment data.

Clinical pathway repository 102 is configured to store pre-existing clinical pathways corresponding to a set of ICD codes. Pre-existing clinical pathways are the clinical pathways defined based on data collected from medical procedures followed in the treatment of diseases corresponding to the set of ICD codes. Clinical pathway repository 102 is further configured to store SOPs and corresponding pre-existing clinical pathways associated with ICD codes.

In an embodiment of the present invention, clinical pathway repository 102 is a digital data repository, wherein data is stored as digital data. Further, the data can be accessed via data processing units such as, but not limited to, desktops, laptops, palmtops, mobile phones and personal digital assistants.

Patient data repository 104 is configured to store patient data of one or more patients. In an embodiment of the present invention, patient data repository is a digital data repository. Patient data includes patient historical data, patient demographic data and patient diagnostic data.

Patient historical data includes details related to patient's medical history and treatment such as, but not limited to, the patient's past and present health status, family healthcare history, immunization history, patient's growth chart and developmental history, medical examination history, medication and medical allergies history. Typically, the patient historical data is collected from the patient's past medical charts and reports. In an embodiment of the present invention, the patient historical data is collected from the patient's medical charts and reports stored in the digital data repositories.

Patient demographic data includes demographic information of the patient such as, but not limited to, date of birth, gender, marital status, address, contact numbers, insurance policy information, communication language and emergency contact information. Typically, patient demographic data is collected from medical charts and records of patients.

Patient diagnostic data includes the information identified during a healthcare professional's diagnosis. The healthcare professional diagnoses the patient during various stages of treatment of the patient. During the initial diagnosis of the patient the healthcare professional examines the patient and assigns an ICD code based on the disease identified in the initial diagnosis. In an embodiment of the present invention, ICD code for a disease is a numeric code. In another embodiment of the present invention, the ICD code for a disease is a text code. In another embodiment of the present invention, the ICD code for a disease is an alphanumeric code. The healthcare professional also prepares one or more reports on the initial diagnosis and diagnostic findings during subsequent medical procedures. The healthcare professional updates the reports for the patient after each diagnosis. Patient diagnostic data further includes the information identified during various medical procedures including medical examinations and medical treatment. For example, patient diagnostic data includes blood test results, X-ray images and so forth. The patient diagnostic data is updated based on the update of information related to the medical procedures.

In an embodiment of the present invention, patient data includes real-time patient data. Real-time patient data represents healthcare information, such as, but not limited to, healthcare professional's diagnosis information, medical examination information and medical treatment information, available without delay post generation. In an embodiment of the present invention, the real-time patient data is collected, stored in a repository, and transmitted electronically via various data processing units. For example, an X-ray image is transmitted in an electronic mail to the related healthcare professional.

Clinical pathway forecasting module 106 is configured to forecast one or more clinical pathways. In an embodiment of the present invention, clinical pathway forecasting module 106 forecasts the clinical pathways based on pre-existing clinical pathways and patient data.

In an embodiment of the present invention, clinical pathway forecasting module 106 predicts possible clinical pathways whenever new data becomes available at any state node. In order to determine the clinical pathways, clinical pathway forecasting module 106 uses analytical models to predict the probability of visiting each of the subsequent state nodes along various clinical pathways. Thereafter, clinical pathway forecasting module 106 determines n-most-likely forecasted clinical pathways, where n≥1 and n is a user-specified number that indicates the number of most-likely pathways to be forecasted.

In another embodiment of the present invention, clinical pathway forecasting module 106 is configured to forecast clinical pathways based on real-time patient data, wherein the clinical pathways are forecasted in real-time.

In another embodiment of the present invention, clinical pathway forecasting module 106 is configured to use analytical models that do not generate probabilistic output, but perform computations for forecasting a single clinical pathway.

In yet another embodiment of the present invention, clinical pathway forecasting module 106 is configured to use analytical models to perform computations for forecasting an initial clinical pathway based on patient data collected from preliminary diagnosis. In another embodiment of the present invention, clinical pathway forecasting module 106 is configured to forecast clinical pathways based on preliminary information available after the first contact between the patient or the patient's escort and the health care facility. Further, the contact can be a physical contact, wherein the patient is diagnosed by a physician or a contact via a communication device such as a mobile phone.

In an embodiment of the present invention, clinical pathway forecasting module 106 forecasts the clinical pathways based on historical patient treatment data stored in patient data repository 104. For example, historical patient treatment data of patients with myocardial infarction is used to forecast clinical pathways for patients with myocardial infarction.

It will be apparent that forecasting performed on the basis of SOPs enables generation of accurate clinical pathways, in various embodiments of the present invention.

In an embodiment of the present invention, clinical pathway forecasting module 106 forecasts the clinical pathways using one or more analytical models such as, but not limited to, regression/time series models, neural network models, belief nets/Bayesian networks and rule engines. In various embodiments of the present invention, the classical probability, i.e. event based probability, is used in rule engines. In an embodiment of the present invention, the analytical models are self-adaptive i.e. the analytical models are designed to get automatically trained to adapt to modifications in data. The analytical models are used to determine the medical procedures required for the treatment of patients. In an embodiment of the present invention, system 100 is self-learning and updates the parameters and threshold values of various functions and analytical models in real-time.

Forecasted clinical pathway repository 108 is configured to store the forecasted clinical pathways. In an embodiment of the present invention, forecasted clinical pathway repository 108 is a digital data repository. In an embodiment of the present invention, digital data repository is one of, but not limited to, a relational database, operational database, analytical database, external database, navigational database and document oriented database.

In various embodiments of the present invention, the clinical pathways are used for forecasting resource requirements of patients over a period of time. The forecast of resource requirements enables a user or a healthcare manager to efficiently manage the resources present in a healthcare organization.

Resource requirement forecasting module 110 is configured to forecast resource requirements at one or more nodes using analytical models including but not limited to, expected resource requirements, minimum and maximum resource requirements and so on for each clinical pathway and the forecasted clinical pathways. In various embodiments of the present invention, resource requirements represent the resources required for treating patients. Examples of resource requirements comprise medications prescribed to patients; equipments for performing medical examinations such as ultrasound and MRI scan; blood culture equipment; technicians; doctors; hospital beds; and so forth. Resource requirement forecasting module 110 forecasts the expected resource requirements, maximum and minimum resource requirements and so on at nodes based on the clinical pathway graphs, forecasted clinical pathways, historical patient treatment data and one or more predetermined analytical models. Examples of the predetermined analytical models include, but not limited to, probabilistic models, regression/time series models, neural network models, belief nets/Bayesian networks and rule engines.

Itinerary generation module 112 is configured to generate itineraries for one or more patients. In an embodiment of the present invention, the itineraries are generated based on the forecasted resource requirements and one or more predetermined analytical models.

An itinerary for a patient provides a patient forecast summary including details related to forecasts for the patient. In an embodiment of the present invention, the itinerary includes forecasts in tabular and graphical forms. The itinerary provides information related to resource requirements of the patient at various states of the clinical pathway.

The itinerary also provides information related to the schedule of medical procedures that the patient is expected to undergo. The schedule of medical procedures includes details such as, but not limited to, expected start time of medical procedures, expected completion time of medical procedures, expected resource requirement times and expected length of stay of the patient. In an embodiment of the present invention, the resource requirements are forecasted using the analytical models.

In an embodiment of the present invention, itinerary generation module 112 is configured to generate one or more itineraries for resources. Each itinerary for resources comprises at least one of utilization status of resources at a given time instance and utilization level of resources. For example, an itinerary for resources may include the number of medicines available, the equipments that are in use, availability of operation theatres, availability of doctors and specialists etc.

In an embodiment of the present invention, system 100 is configured to generate clinical pathway graphs for clinical pathways. A clinical pathway graph is a collection of nodes and interconnections, wherein nodes include state nodes, action nodes and decision nodes. Each node is associated with one or more functions defined based on various analytical models. In an embodiment of the present invention, system 100 is configured to forecast clinical pathways based on ordered graphs. In another embodiment of the present invention, system 100 is configured to forecast clinical pathways based on partially ordered graphs. The forecasting of clinical pathways can be performed based on sequence dependent as well as sequence independent processes during the medical treatment process.

State nodes represent states in the clinical pathway. State nodes are associated with state functions, which specify the data recorded for the corresponding state. For example, state functions define the actions to be invoked during the stage of treatment by specifying the action nodes associated with the state node to be invoked. Further, the state functions define communication of information with other nodes and invoking the next state node with the updated patient information.

Each state node has an action node associated with it, which depicts the actions performed in that state of the clinical pathway. Action nodes are one of information nodes, resource nodes, and information and resource nodes. Various actions are performed in the treatment of a patient. For example, an X-ray image of the patient is taken; blood tests are performed on patients and so forth. Information nodes represent information generation points on the clinical pathway. For example, the information node associated with a fibrinolysis state node represents the fibrinolysis parameters that need to be stored during fibrinolysis. Resource nodes represent points on the clinical pathway where resources are consumed. For example, the resource node associated with fibrinolysis represents the resources that are required for performing fibrinolysis. Information nodes represent points on the clinical pathway where information is generated. Information and resource nodes represent points on the clinical pathway where both information is generated and resources are consumed. Information nodes are associated with information functions, resource nodes are associated with resource functions and information and resource nodes are associated with both an information function and a resource function. Information functions specify information generated by the action depicted by the action node. Resource functions specify the resources utilized by the action depicted by the action node. The information function and resource function use patient data as input.

Decision nodes represent decision points in the clinical pathway, wherein updated patient data is used at each decision point to determine subsequent states. Decision nodes are associated with decision functions, which are used to determine the subsequent states. For example, a decision node for determination whether a fibrinolysis would be required is associated with decision functions including parameters for evaluating whether fibrinolysis is required. Decision functions include a set of decision variables, which is a sub-set of patient data values available at the decision node.

The interconnections in clinical pathway graphs represent connections between state nodes, action nodes and decision nodes. Interconnections depict transformation of information or consumption of resources over the clinical pathway graph.

The transition of information is depicted using various types of transitions. A transition can depict transition of information via an information node, wherein additional information is appended to the existing information. A transition can also depict traversal of information from one state node to another state node without any transformation, when the information is being transmitted to a resource node. Transitions can also depict the start/termination or end of the clinical pathway.

Figure 2:
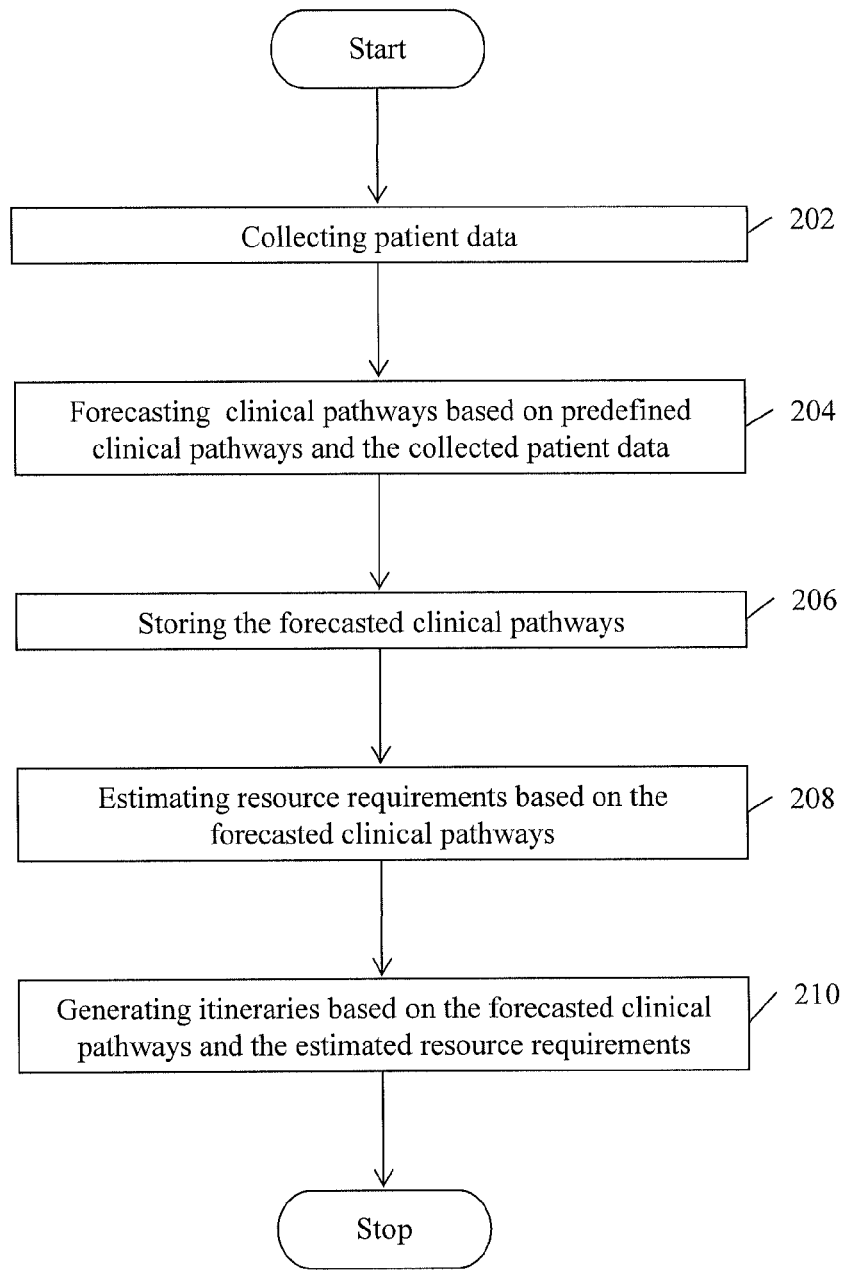
FIG. 2 illustrates a flowchart of a method for forecasting one or more clinical pathways, in accordance with an embodiment of the invention.

FIG. 2 illustrates a flowchart of a method for forecasting one or more clinical pathways, in accordance with an embodiment of the present invention.

At step 202, patient data for one or more patients is collected, wherein patient data includes patient historical data, patient demographic data and patient diagnostic data. In an embodiment of the present invention, the patient data includes real-time patient data.

At step 204, the one or more clinical pathways are forecasted. In an embodiment of the present invention, the clinical pathways are forecasted based on pre-existing clinical pathways and the collected patient data. The pre-existing clinical pathways are identified based on the ICD code assigned during initial diagnosis of patients. Thereafter, one or more analytical models such as, but not limited to, regression/time series models, neural network models, belief nets and rule engines, are used for forecasting clinical pathways. The analytical models are applied on the collected patient data to forecast the clinical pathways for patients. In an embodiment of the present invention, the analytical models are applied on one or more states of pre-existing clinical pathways to forecast the states and sequence of states in clinical pathways of patients.

In an embodiment of the present invention, the clinical pathways are forecasted based on real-time patient data. The real-time patient data is collected via one or more data processing units. The patient data is updated based on the real-time patient data collected via the data processing units. Data processing units process captured data encoded in a format recognizable by the data processing unit or has been created and stored. Examples of data processing units include, but are not limited to, computers, laptops, personal digital assistants, palmtops and mobile phones. The updated patient data is used for forecasting the clinical pathways. It will be apparent that real-time patient data based forecasting of clinical pathways provide healthcare professionals with real-time forecasts about clinical pathways of patients, thereby aiding the healthcare professionals in taking decisions for treatment of patients.

In an embodiment of the present invention, Standard Operating Procedures (SOPs) are used for forecasting the clinical pathways for patients. In another embodiment of the present invention, clinical pathway graphs are used for forecasting the clinical pathways for patients. The pre-existing clinical pathways are used to identify the states that may be present in the forecasted clinical pathways. The analytical models are applied on the identified states to forecast the subsequent states in the clinical pathways.

At step 206, the forecasted clinical pathways are stored. In an embodiment of the present invention, the forecasted clinical pathways are stored in a digital data repository.

At step 208, resource requirements for patients are forecasted. In various embodiments of the present invention, the forecasting is performed using one or more predetermined analytical models. Further, the forecasting is based on the clinical pathway graphs, forecasted clinical pathways and historical treatment data of patients.

At step 210, one or more itineraries are generated. In an embodiment of the present invention, the itineraries are generated based on the forecasted resource requirements and one or more predetermined analytical models. In an embodiment of the present invention, the itinerary of a patient includes resource requirements and details related to the time schedule of treatment for the patient.

The time schedule of treatment is generated by calculating time schedules at states on the clinical pathway. At each state the expected time of arrival and departure is computed based on analytical functions. The expected time of arrival at a state is the time at which the patient is expected to enter the state and the expected time of departure is the time at which the medical procedures in the state are completed. In an embodiment of the present invention, the itinerary is updated based on the updated patient data in real-time. For example, the itinerary is updated based on blood test results, inferences on X-ray images and so forth.

Figure 3:
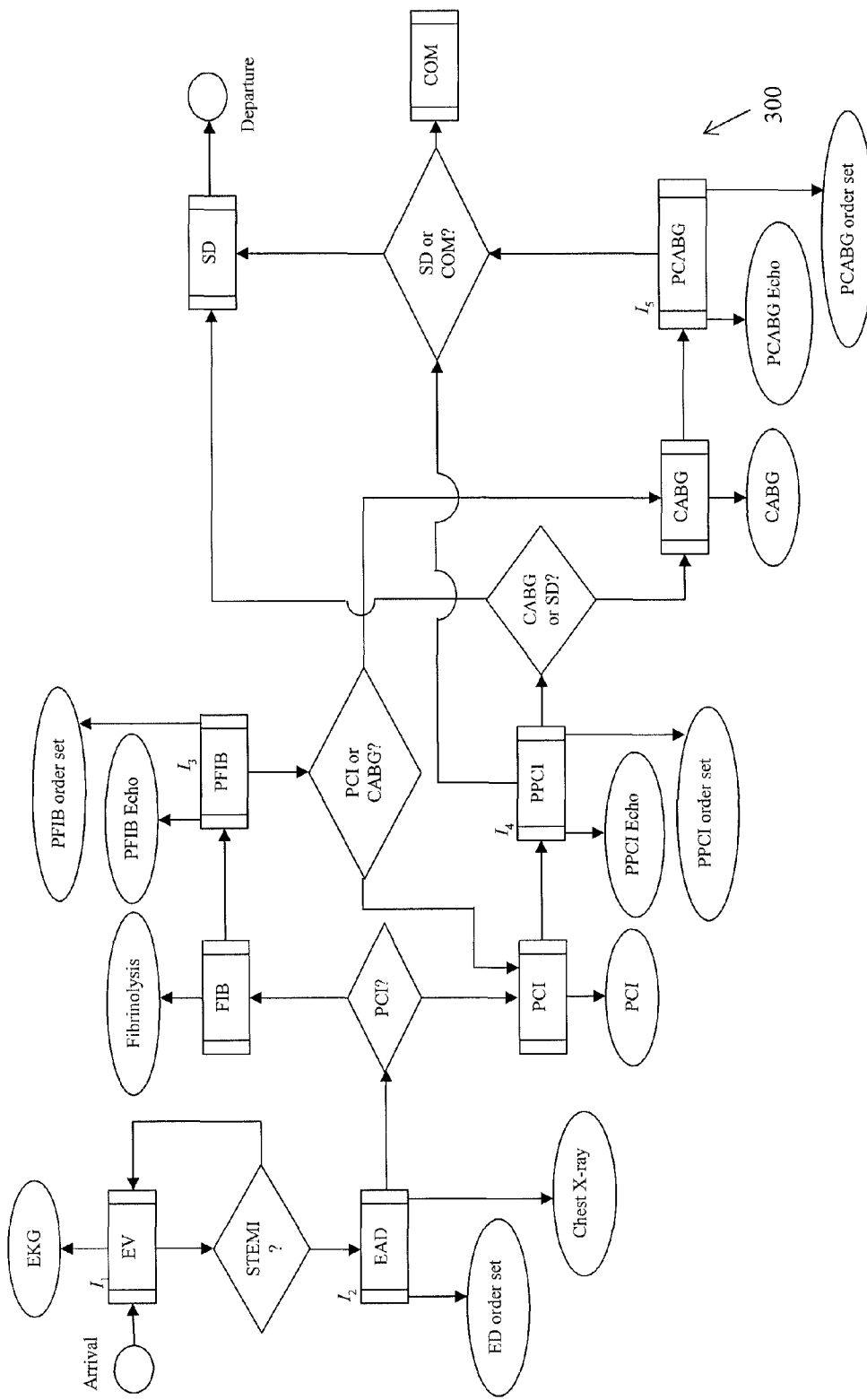
FIG. 3 illustrates an exemplary Standard Operating Procedure (SOP) graph.

The forecasting of the expected time of arrival and departure is performed by calculating finish times at each state node. In an embodiment of the present invention, the finish time at the first state node ($SN_1$) (for example EV, as illustrated in FIG. 3) is provided by:

$$FT_{p1} = AT_p + TL_1 + TD_1;$$

wherein, $FT_{p1}$ is the finish time of patient p (p=1, 2, ..., P, wherein P is the total number of patients) at $SN_1$, $AT_p$ is the arrival time of the patient at $SN_1$, $TL_1$ is the time constraint lower bound at $SN_1$ and $TD_1$ is time duration to perform the action at $SN_1$. The time constraint lower bound is the time delay due to medical constraints such as waiting time before performing medical procedures. It will be apparent that the finish time can be calculated using various models and need not be limited to the model described above.

In accordance with an embodiment of the present invention, the finish time at state node j ($SN_j$) is provided by:

$$FT_{pj} = FT_{pj-1} + \max\{t_{ij}; TL_j\} + TD_j;$$

wherein, $FT_{pj}$ is the finish time at $SN_j$; $FT_{pj-1}$ is the finish time at state node j−1 ($SN_{j-1}$); $t_{ij}$ is the average time taken by the patient to travel from one state node to another state node (i=1, 2, ..., J−1 and j=2, 3, ..., J, wherein J is the total number of state nodes); $TL_j$ is the time constraint lower bound at $SN_j$ and $TD_j$ is the time duration to perform the action at $SN_j$. It will be apparent that the finish time at $SN_j$ can be calculated using various models and need not be limited to the model described above.

The finish time calculated for each state of the clinical pathway is used to determine the time schedule of the patient. The time schedule includes details related to the expected time of arrival and departure of the patient for various states. The time schedule determined for various patients is used to determine waiting time of the patient at the states, number of patients using a resource at a given time instance, utilization status of resources at a given time instance and utilization level of resources.

FIG. 12 is In an embodiment of the present invention, the waiting time for a patient is calculated based on the following equation:

$$WT_{pj} = FT_{pj} - [\max\{FT_{pj-1}; t_{ij}; TL_j\}];$$

wherein, $WT_{pj}$ represents the waiting time of patient p at state node j. It will be apparent that the waiting time can be calculated using various models and need not be limited to the model described above.

In an embodiment of the present invention, the resource utilization is calculated based on the following equation:

$$RU_k = \left[\frac{\sum_{p=1}^{P} TS_{pk}}{AvT_k}\right] \times 100, \forall k.$$

In the above equation, $RU_k$ is the percentage resource utilization of resource k, $TS_{pk}$ is the time a patient p seized the resource k, and $AvT_k$ is the time a resource k is available in a given day. It will be apparent that the percentage of resource utilization can be calculated using various models and need not be limited to the model described above.

In an embodiment of the present invention, itineraries generated comprise the utilization status of resources and the utilization level of resources.

FIG. 3 illustrates an exemplary Standard Operating Procedure (SOP) graph. The exemplary SOP graph represents a STEMI (ST segment Elevation Myocardial Infarction) pathway.

The first state in the clinical pathway graph is an Evaluation before Diagnosis (EV) state associated with an EV state node. The EV state node is associated with an information function ($I(.)$) and a resource function. The variables of the information function are:

Response variable: Electrocardiography (EKG); and

Regressor variables: Age, Smoker, Obese, Clinical Symptom 1 (CS 1), Clinical Symptom 2 (CS 2), Clinical Symptom 3 (CS 3), Pulse High and BP Low.

The information function is defined based on a logistic regression model or multinomial logistic regression model. The resource function defines the resources that are required for EKG. The patient data is used to forecast all the subsequent states in the clinical pathway for the patient using the information functions and decision functions at subsequent action and decision nodes.

The EV state node is connected to a decision node for determining whether a patient is suffering from STEMI or not. A rule based engine is used to determine whether or not the patient should be sent to state Evaluation after Diagnosis (EAD). The rule based engine defines the decision function at the decision node. The decision function is:

If $I_1(.) >= 0.5$, then go to EAD.

The function is applied on the patient data to forecast whether the next state is EAD or not.

The state node EAD is associated with an information function ($I_2(.)$) and a resource function. The variables of the information function are:

Response variable: Chest X-ray; and

Regressor variables: age, smoker, obese, CS 1, CS 2, CS 3, Pulse High and BP Low.

The information function is defined based on a logistic regression model. The resource function defines the resources that are required for performing EKG, Activated Partial Thromboplastin Time (APTT), International Normalized Ratio (INR), Echo Cardiogram (Echo), X-Ray and Angiogram.

The state node EAD is associated with a decision node for determining whether a Percutaneous Coronary Intervention (PCI) or Fibrinolysis (FIB) is required. A rule based engine is used to determine whether the patient needs to undergo PCI or FIB. The determination is based on the patient data.

If the decision is made to send the patient to PCI, the resource function associated with the state node PCI determines the resource requirement to perform PCI. Then, the patient is sent to the next state node Post PCI monitoring.

The Post PCI monitoring state node is associated with an information function and a resource function. The variables of the information function are:

Response variable: Post PCI Echo/Shock on Echo; and

Regressor variables: Age, Smoker, Obese, CS 1, CS 2, CS 3, Pulse High, BP Low, Shock on Echo on Post FIB Monitoring/Post FIB Echo, CHF on X-ray, EKG.

The information function is based on a logistic regression model. Alternately the information function considers:

Dependent variable: probability of patient to undertake step down monitoring after post PCI monitoring ($P_{PPCI}$); and Independent variable: total number of patients undergone post PCI monitoring.

The information function is based on a simple probability model based on occurrence frequency. Further $P_{PPCI}$ is calculated using simple classical probability as follows:

$$P_{PPCI} = NS/TN;$$

wherein, NS represents the number of patients that underwent step down monitoring after undergoing post PCI monitoring and TN represents the total number of patients that had undergone post PCI monitoring.

For each node in the clinical pathway graph a similar methodology is followed. At each node the patient data is considered to forecast the subsequent states. The computations required to solve the analytical functions and statistical models are carried out by built-in algorithms embedded in the analytical engine. The clinical pathway forecasting module considers the computed parameters to forecast the clinical pathway of the patient. The predicted pathway is used to forecast the time schedule for the patient by the itinerary generation module.

In various embodiments of the present invention, the parameters present in the linear regression models and non-linear regression models such as log-linear models, logistic regression models, and multinomial logistic regression models, are estimated based on, but not limited to, ordinary least-squares, maximum log-likelihood estimates (MLE) and numerical techniques. The validation of the parameters and the corresponding models is performed by computing statistics such as, but not limited to, chi-square statistics (Pearson and deviation method), Somers' D and Kendall's Tau-a statistics. In addition, the parameters in the model can also be estimated for parametric and non-parametric empirical methods.

In various embodiments of the present invention, graphical models such as Bayesian networks are used to exploit the casual and dependency structure of the domain for which clinical pathways are being forecasted. The parameters for conditional probability tables (CPTs) are learned from historical data using techniques such as MLE. Thereafter, inference is drawn using one or more predetermined algorithms such as the junction tree algorithm, Pearl's algorithm etc.

In various embodiments of the present invention, neural networks are applied if the underlying distribution of the data is unknown. Different neural network models such as single and multi-layer perceptrons, radial basis function, recurrent networks, and time-delay networks are employed to compute the required output at each node. The network parameters such as link weights are learnt from patient data using the standard neural network algorithm such as the perceptron algorithms, the back propagation algorithms, and conjugate gradient descent algorithms.

In various embodiments of the present invention, a rule engine is used at decision nodes. The rule engine comprises logical rules as well as soft probabilistic/evidential rules that are based on evidential or probabilistic information. In addition, the rule engine uses both forward and backward inferences for arriving at decisions in decision nodes.

In various embodiments of the present invention, decision trees are used to decide which alternative node/path can be selected at a decision node. The decision may be based on an expected value for determining the alternative node/path. The expected value is a criterion that considers both the possible outcomes and the probability of each outcome. The expected value can be computed based on simple probabilistic models.

Figure 4A:
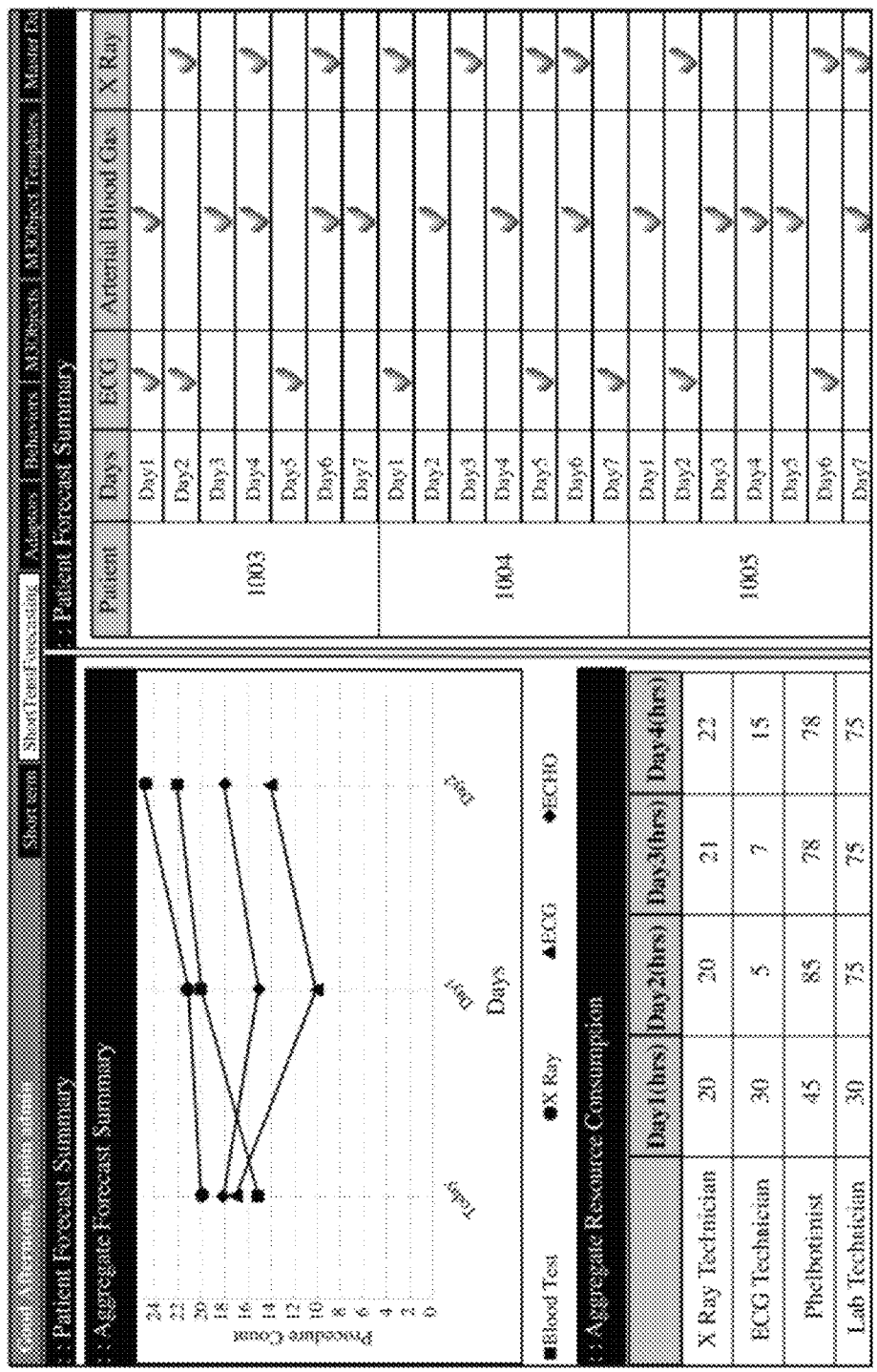
FIGS. 4A and 4B illustrate exemplary screenshots of the system for forecasting one or more clinical pathways.
Figure 4B:
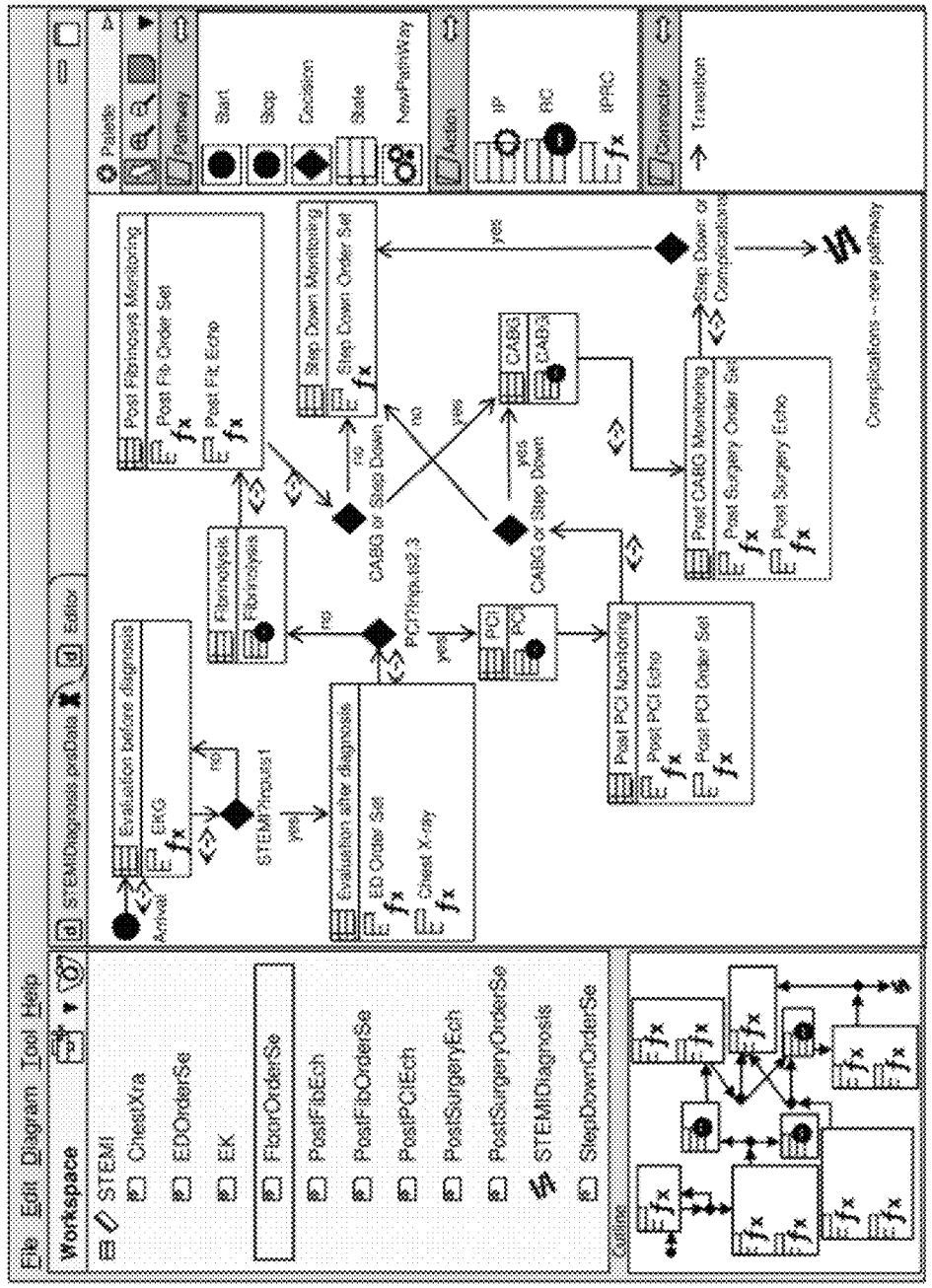

FIGS. 4A and 4B illustrate exemplary screenshots of the system for forecasting one or more clinical pathways.

FIG. 4A illustrates an exemplary screenshot of the system for forecasting one or more clinical pathways.

The exemplary screenshot provided illustrates a post login administrator view. In order to access the system a user needs to input login credentials for authentication. The user is provided with a corresponding Graphical User Interface (GUI) after the login credentials are authenticated.

The exemplary screenshot illustrates the GUI loaded for an administrator. The administrator can select one of a set of tabs including Short term tab, Short Term Forecasting tab, Adaptors tab, Behaviors tab, M3Objects, M3Object Templates and so forth. On selection of a tab from the set of tabs the administrator is provided with a set of views. For example, when the Short Term Forecasting tab is selected as illustrated in the exemplary screenshot, the administrator can view Patient Forecast Summary. Further, Patient Forecast Summary is provided in tabular as well as graphical form.

Patient Forecast Summary includes Aggregate Forecast Summary, Aggregate Resource Consumption and a tabular display of Patient Forecast Summary. Aggregate Forecast Summary provides the administrator with a graphical display of the resource requirements such as the forecast of the number of blood tests to be conducted, the forecast of the number of X-Rays to be conducted and so forth. Aggregate Resource Consumption provides the resource consumption details in tabular form. For example, the Aggregate Resource Consumption provides the number of hours for which an X-Ray Technician is required, the number of hours an ECG Technician is required and so forth.

The tabular display of Patient Forecast Summary provides the resource requirements for each patient. For example, the tabular display provides the resource requirements for patient 1003, as shown in the screenshot, wherein the patient 1003 is expected to undergo an ECG and Arterial Blood Gas test on Day 1, an ECG and X-Ray examination on Day 2 and so forth.

It will be apparent that the options provided to a user are not limited to the options illustrated in the exemplary screenshot.

FIG. 4B illustrates another exemplary screenshot of the system for forecasting one or more clinical pathways.

The exemplary screenshot illustrates a STEMI SOP graph. As illustrated, a user is provided with a workspace, an outline view, a view of the clinical pathway, pathway options, action options and connector options for performing one or more operations.

The workspace provides the nodes in the clinical pathway such as ChestXray, EDOrderSet, EK and so forth. On selection of a node the user is provided with a view of the clinical pathway corresponding to the selected node. The outline view provides the outline of the clinical pathway graph. The pathway options provide the user with pathway and node defining options, wherein the user can define new pathways, state nodes, decision nodes and so forth using the provided options. The action options as shown in the screenshot provide options to users for defining actions. For example, the user can define the information to be generated at a node, the resource to be consumed at a node and so forth. The connector options provide options for connecting nodes using various connectors. For example, the user can connect the nodes using a transition.

It will be apparent that the options provided by the system for defining the clinical pathway graph are not limited to the options illustrated in the exemplary screenshot.

The present invention may be implemented in numerous ways including as a apparatus, method, or a computer program product such as a computer readable storage medium or a computer network wherein programming instructions are communicated from a remote location.

Various embodiments of the present invention, may be implemented via one or more computer systems. The computer system includes at least one processing unit and memory. The processing unit executes program instructions and may be a real or a virtual processor. The computer system is not intended to suggest any limitation as to scope of use or functionality of described embodiments. Typical examples of a computer system include a general-purpose computer, a programmed microprocessor, a micro-controller, a peripheral integrated circuit element, and other devices or arrangements of devices that are capable of implementing the steps that constitute the method of the present invention. In an embodiment of the present invention, the memory may store software for implementing various embodiments of the present invention.

The present invention may suitably be embodied as a computer program product for use with a computer system. The method described herein is typically implemented as a computer program product, comprising a set of program instructions which is executed by a computer system or similar device. The set of program instructions may be a series of computer readable codes stored on a tangible medium, such as a computer readable storage medium, for example, diskette, CD-ROM, ROM, or hard disk, or transmittable to a computer system, via a modem or other interface device, over either a tangible medium, including but not limited to optical or analogue communications lines. The implementation of the invention as a computer program product may be in an intangible form using wireless techniques, including but not limited to microwave, infrared, bluetooth or other transmission techniques. These instructions can be preloaded into a system or recorded on a storage medium such as a CD-ROM, or made available for downloading over a network such as the Internet or a mobile telephone network. The series of computer readable instructions may embody all or part of the functionality previously described herein.

While the exemplary embodiments of the present invention are described and illustrated herein, it will be appreciated that they are merely illustrative. It will be understood by those skilled in the art that various changes in form and detail may be made therein without departing from or offending the spirit and scope of the invention.

What is claimed is:

1. A system for forecasting one or more clinical pathways and resource requirements of at least one patient, the system comprising:
    a processor;
    an input module, in communication with a computer system, configured to receive inputs pertaining to patient diagnostic data, the patient diagnostic data comprising information identified during diagnosis of the patient;
    a repository, in communication with the computer system, configured to store data, the data comprising:
        patient data comprising at least one of:
            the patient diagnostic data received from the input module;
            patient historical data comprising historical treatment data of the patient; and
            patient demographic data comprising demographic details of the patient; and
        pre-existing clinical pathways relevant to the patient data, wherein each pre-existing clinical pathway comprises a sequence of states defined based on data previously collected from medical procedures followed in treatment of a disease state consistent with the patient data, and wherein each state within the sequence of states represents a stage of medical treatment;
    a clinical pathway forecasting module, in communication with the computer system, configured to forecast one or more clinical pathways by application of one or more predetermined analytical models on the patient data and the pre-existing clinical pathways; and
    a resource requirement forecasting module, in communication with the computer system, configured to forecast the resource requirements of the patient based on the pre-existing clinical pathways, the one or more forecasted clinical pathways, historical data relevant to treatment of other patients having a disease state consistent with the patient data, and one or more predetermined analytical models.

2. The system of claim 1, wherein the clinical pathway forecasting module is further configured to forecast an initial clinical pathway based on at least one of:
    information identified during the initial diagnosis of the patient;
    preliminary information gathered during the initial contact with the patient; and
    the pre-existing clinical pathways.

3. The system of claim 2, wherein the resource requirement forecasting module is further configured to forecast the resource requirements based on at least one of:
    patient historical data;
    the pre-existing clinical pathways and forecasted clinical pathways;
    the initial forecasted clinical pathway; and
    at least one predetermined analytical model.

4. The system of claim 2 further comprising an itinerary generation module, in communication with the computer system, configured to generate one or more itineraries based on at least one of:
    the pre-existing clinical pathways and forecasted clinical pathways;
    the initial forecasted clinical pathway;
    the forecasted resource requirements;
    arrival time of the patient;
    average time taken by the patient to travel from one state to another state of the clinical pathway;
    time duration for performing procedures at each state;
    scheduled waiting times prior to performing procedures at each state; and
    at least one predetermined analytical model;
    wherein each itinerary comprises a schedule for treatment of the patient.

5. The system of claim 4, wherein the schedule for treatment of the patient is determined by calculating time required at one or more states of the clinical pathway.

6. The system of claim 4, wherein the schedule for treatment of the patient is used to determine at least one of:
    waiting time of the patient at each state;
    number of patients using a resource at a given time instance;
    utilization status of resources at a given time instance and utilization level of resources.

7. The system of claim 4, wherein the generated itineraries are stored in the repository.

8. The system of claim 4, wherein the itinerary generation module is further configured to generate one or more itineraries for resources, each itinerary for resources comprising at least one of:
    utilization status of resources at a given time instance; and
    utilization level of resources.

9. The system of claim 1, wherein the clinical pathway forecasting module is further configured to forecast the clinical pathways based on real-time data pertaining to the patient gathered via the input module.

10. The system of claim 1 further comprising a clinical pathway graph module, in communication with the computer system, configured to generate one or more clinical pathway graphs, wherein each graph represents a clinical pathway and comprises one or more nodes connected via one or more interconnections.

11. The system of claim 10, wherein the clinical pathway graph module is further configured to generate one or more clinical pathway graphs for each forecasted clinical pathway.

12. The system of claim 10, wherein each node is at least one of:
a state node representing a state in the forecasted clinical pathway, the state node being associated with predefined state functions for ascertaining data recorded for the corresponding state;
an action node representing an action being performed, the action node being associated with at least one of a predefined information function and a predefined resource function corresponding to the action being performed; and
a decision node representing a decision point in the forecasted clinical pathway, the decision node being associated with one or more predefined decision functions for determining subsequent states corresponding to the decision point.

13. The system of claim 1, wherein the clinical pathway forecasting module, in communication with the computer system, is configured to compute at least one of:
probability of visiting each of the subsequent state nodes along one or more clinical pathways;
predicted outcome; and
value of dependent variables;
wherein the computations are performed at one or more nodes of the pre-existing clinical pathways and the forecasted clinical pathways.

14. The system of claim 13, wherein the computations are performed to forecast one or more clinical pathways based on data available at one or more states of the clinical pathway.

15. The system of claim 1 further comprising a forecasted clinical pathway repository, in communication with the computer system, configured to store the forecasted clinical pathways.

16. The system of claim 1 further comprising a clinical pathway repository, in communication with the computer system, configured to store at least one of:
the pre-existing clinical pathways, wherein the pre-existing clinical pathways provide guidelines for treatment of diseases corresponding to a set of International Classification of Diseases (ICD); and
one or more Standard Operating Procedures (SOPs) defined for the set of ICD.

17. The system of claim 1 further comprising a patient data repository, in communication with the computer system, configured to store the patient data.

18. The system of claim 1, wherein at least one of the predetermined analytical models is adaptive.

19. The system of claim 1, wherein the clinical pathway forecasting module is configured to forecast the one or more clinical pathways by predicting probabilities of occurrence of each state in the pre-existing clinical pathways, based on the gathered patient data.

20. The system of claim 19, wherein forecasting the one or more clinical pathways further comprises determining n most likely forecasted clinical pathways, wherein n is a operator specified number such that n≥1.

21. A computer-implemented method for forecasting one or more clinical pathways and resource requirements of at least one patient, the method comprising:
gathering, by a computer system, inputs pertaining to patient data, the patient data comprising at least one of:
patient diagnostic data comprising information identified during diagnosis of the patient;
patient historical data comprising historical treatment data of the patient; and
patient demographic data comprising demographic details of the patient;
retrieving, by the computer system, pre-existing clinical pathways relevant to the gathered patient data, wherein each pre-existing clinical pathway comprises a sequence of states defined based on data previously collected from medical procedures followed in treatment of a disease state consistent with the gathered patient data, and wherein each state within the sequence of states represents a stage of medical treatment;
forecasting, by the computer system, one or more clinical pathways by application of one or more predetermined analytical models on the gathered patient data and the retrieved pre-existing clinical pathways; and
forecasting, by the computer system, the resource requirements of the patient based on the pre-existing clinical pathways, the one or more forecasted clinical pathways, historical data relevant to treatment of other patients having a disease state consistent with the patient data, and one or more predetermined analytical models.

22. The computer-implemented method of claim 21 further comprising forecasting, using the computer system, the clinical pathways based on real-time data pertaining to the patient.

23. The computer-implemented method of claim 21 further comprising storing, using the computer system, the forecasted clinical pathways.

24. The computer-implemented method of claim 21 further comprising forecasting, using the computer system, an initial clinical pathway for the patient based on at least one of:
information identified during the initial diagnosis of the patient;
preliminary information gathered during the initial contact with the patient; and
the pre-existing clinical pathways.

25. The computer-implemented method of claim 24 further comprising generating, using the computer system, one or more itineraries for the patient based on at least one of:
the pre-existing clinical pathways and forecasted clinical pathways;
the initial forecasted clinical pathway;
the forecasted resource requirements;
arrival time of the patient;
average time taken by the patient to travel from one state to another state of the clinical pathway;
time duration for performing procedures at each state;
scheduled waiting times prior to performing procedures at each state; and
at least one predetermined analytical model;
wherein each itinerary comprises a schedule for treatment of the patient.

26. The computer-implemented method of claim 25, wherein the schedule for treatment of a patient is determined by forecasting time required at one or more states of the clinical pathway.

27. The computer-implemented method of claim 21, wherein forecasting the one or more clinical pathways comprises predicting probabilities of occurrence of each state in the pre-existing clinical pathways, based on the gathered patient data.

28. The computer-implemented method of claim 27, wherein forecasting the one or more clinical pathways further comprises determining n most likely forecasted clinical pathways, wherein n is a operator specified number such that n≥1.

29. A computer program product comprising a non-transitory computer usable medium having a computer-readable program code embodied thereon to forecast one or more clinical pathways and resource requirements of at least one patient, the computer-readable program code comprising instructions that, when executed by a computer system, cause the computer system to:
- gather inputs pertaining to patient data, the patient data comprising at least one of:
  - patient diagnostic data comprising information identified during diagnosis of the patient;
  - patient historical data comprising historical treatment data of the patient; and
  - patient demographic data comprising demographic details of the patient;
- retrieve pre-existing clinical pathways relevant to the gathered patient data, wherein each pre-existing clinical pathway comprises a sequence of states defined based on data previously collected from medical procedures followed in treatment of a disease state consistent with the gathered patient data, and wherein each state within the sequence of states represents a stage of medical treatment;
- forecast one or more clinical pathways by application of one or more predetermined analytical models on the gathered patient data and the retrieved pre-existing clinical pathways; and
- forecast the resource requirements of the patient based on the pre-existing clinical pathways, the one or more forecasted clinical pathways, historical data relevant to treatment of other patients having a disease state consistent with the patient data, and one or more predetermined analytical models.

30. The computer program product of claim 29 further comprises instructions that, when executed by the computer system, cause the computer system to forecast the clinical pathways based on real-time data pertaining to the patient.

31. The computer program product of claim 29 further comprises instructions that, when executed by the computer system, cause the computer system to store the forecasted clinical pathways.

32. The computer program product of claim 29 further comprises instructions that, when executed by the computer system, cause the computer system to forecast an initial clinical pathway for the patient based on at least one of:
- information identified during the initial diagnosis of the patient;
- preliminary information gathered during the initial contact with the patient; and
- the pre-existing clinical pathways.

33. The computer program product of claim 32 further comprises instructions that, when executed by the computer system, cause the computer system to generate one or more itineraries for the patient based on at least one of:
- the pre-existing clinical pathways and forecasted clinical pathways;
- the initial forecasted clinical pathway;
- the forecasted resource requirements;
- arrival time of the patient;
- average time taken by the patient to travel from one state to another state of the clinical pathway;
- time duration for performing procedures at each state;
- scheduled waiting times prior to performing procedures at each state; and
- at least one predetermined analytical model;

wherein each itinerary comprises a schedule for treatment of the patient.

34. The computer program product of claim 33, wherein the schedule for treatment of a patient is determined by forecasting time required at one or more states of the clinical pathway.

35. The computer-implemented method of claim 29, wherein forecasting the one or more clinical pathways comprises predicting probabilities of occurrence of each state in the pre-existing clinical pathways, based on the gathered patient data.

36. The computer-implemented method of claim 35, wherein forecasting the one or more clinical pathways further comprises determining n most likely forecasted clinical pathways, wherein n is a operator specified number such that n≥1.

* * * * *